United States Patent [19]

Gross et al.

[11] Patent Number: 5,306,308
[45] Date of Patent: Apr. 26, 1994

[54] INTERVERTEBRAL IMPLANT

[76] Inventors: Ulrich Gross, Hindenburgdamm 30, W-1000 Berlin 45; Herman-Josef Schmitz, Fronhofer Str. 14, W-1000 Berlin 41; Bertram Kaden, Cranachstr 7, W-1000 Berlin 41; Gerhard Fuhrmann, Bertholdstr. 3, W-1000 Berlin 37, all of Fed. Rep. of Germany

[21] Appl. No.: 848,955
[22] PCT Filed: Oct. 23, 1990
[86] PCT No.: PCT/DE90/00819
§ 371 Date: Apr. 23, 1992
§ 102(e) Date: Apr. 23, 1992
[87] PCT Pub. No.: WO91/05521
PCT Pub. Date: May 2, 1991

[30] Foreign Application Priority Data

Oct. 23, 1989 [DE] Fed. Rep. of Germany ....... 8912648

[51] Int. Cl.⁵ .............................................. A61F 2/44
[52] U.S. Cl. ........................................ 623/17; 606/61
[58] Field of Search ....................... 623/16, 17; 606/61

[56] References Cited

U.S. PATENT DOCUMENTS

| | | | |
|---|---|---|---|
| 4,863,477 | 9/1989 | Monson | 623/17 |
| 4,865,603 | 9/1989 | Noiles | |
| 5,015,247 | 5/1991 | Michelson | 623/17 |

FOREIGN PATENT DOCUMENTS

| | | |
|---|---|---|
| 2263842 | 7/1974 | Fed. Rep. of Germany . |
| 2804936 | 8/1979 | Fed. Rep. of Germany . |
| 9000037 | 1/1990 | PCT Int'l Appl. . |
| 672589 | 12/1989 | Switzerland . |

*Primary Examiner*—David Isabella
*Assistant Examiner*—Debra S. Brittingham
*Attorney, Agent, or Firm*—Spencer, Frank & Schneider

[57] ABSTRACT

An intervertebral implant consisting of a disc-shaped spacer made of rigid material and insertable between opposed and adjacent vertebrae in which the opposing sides (1, 2) of the implant bordering the vertebrae are circular discs and have a central raised dome (3 or 4) and roof-shaped projections thereon (5 or 6).

16 Claims, 5 Drawing Sheets

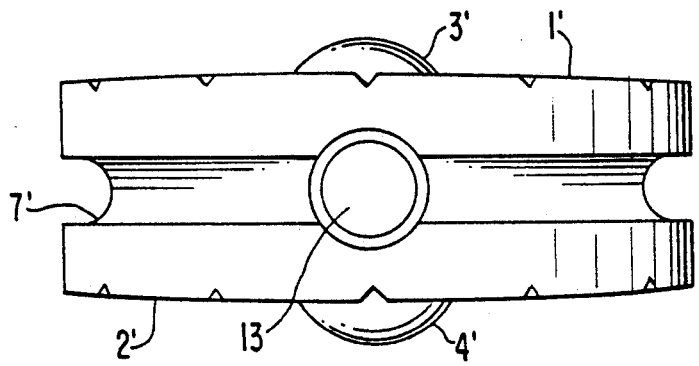
FIG. 4c
FIG. 4a
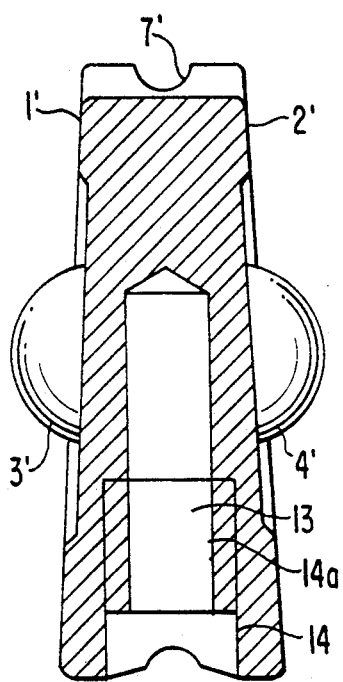
FIG. 4b
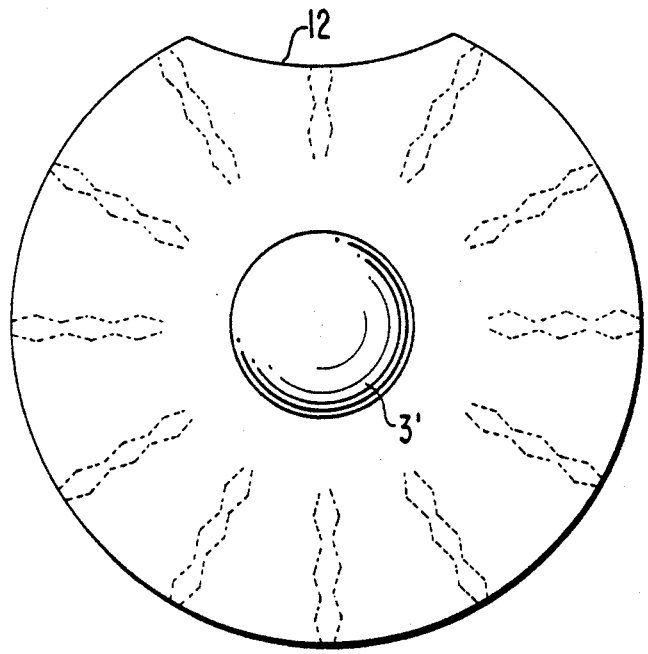
FIG. 4d
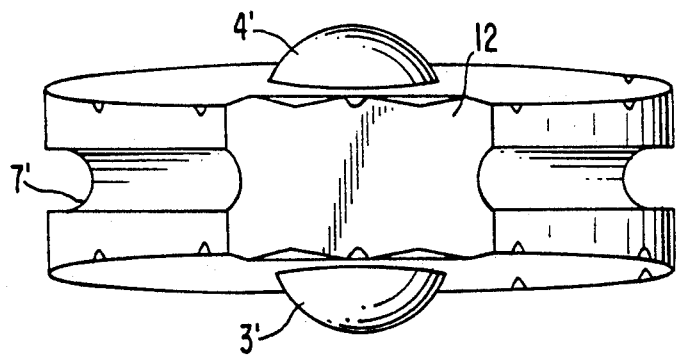

INTERVERTEBRAL IMPLANT

SUMMARY OF THE INVENTION

The invention relates to a intervertebral implant comprising a disc made of rigid material and having two opposing sides bordering respectively adjacent vertebrae. Each of the opposing sides includes a circular frontal area and a raised dome at the central portion thereof. The opposing sides further include roof shaped projections surrounding the raised dome, each of these projections having a pair of end faces, and a ridge edge and a pair of base edges extending between the end faces. The base edges and the ridge edge of these projections form respective areas of concentric circles.

German Offenlegungsschrift (published patent application) 28 04 936 and German Offenlegungsschrift (published patent application) 22 63 842, for instance, describe such a known endoprosthesis.

A drawback with such known endoprostheses is that in order to anchor them firmly to the vertebra either a complicated endoprosthesis shape and a corresponding milling of the bone or the use of bone cement is necessary.

The achievable protection against rotation or sideward dislocation is generally problematic due to the large mechanical strain exerted on the spine.

It is therefore an object of the invention to provide an endoprothesis of the intervertebral disc which provides a good and long-lasting fit between the vertebrae and with which micromovements and in particular rotations and sideward dislocation can be prevented.

The invention is based on the realization that the sideward dislocation of an intervertebral implant can be reliably prevented by a number of geometrical shaping measures whereby this shaping, in the case of a round and essentially disc-shaped implant, is such that the stops designed to prevent any movement in a radial and tangential direction are in the form of areas which are essentially oriented in a direction transverse to these radial and tangential directions of movement. The corresponding shaping is in addition such that the parts incorporated in the areas can penetrate the neighbouring vertebrae and are therefore shaped as roof-shaped projections. This penetration increases with the amount of loading applied so that the stopping effect also increases. The surface is also such that it can grow into the vertebrae which have been milled accordingly. The sideward dislocation or rotation of the intervertebral implant must be prevented by the geometrical shaping for at least as long as the implant has started to grow onto the bone.

According to the invention the frontal areas of the endoprosthesis bordering the vertebrae are circular and each comprise a central raised dome and roof-shaped projections whose longitudinal base edges form concentric parts of arcs of circles. The raised dome enables the endoprosthesis to be centered relative to the vertebrae and also helps to stabilize it with regard to sideward dislocations. However, dislocations and rotational movements are mainly prevented from occuring by the projections.

In an advantageous embodiment of the invention both the size and the shape of the raised dome are formed in accordance with the anatomical conditions of the vertebrae, in order that the raised dome can then be firmly pressed into the inner softer tissue of the vertebrae. The raised dome is then preferably convex and spherical in shape.

The roof-shaped projections can be pressed into the spongiosa of the vertebrae so that only one level cut must be carried out on the vertebra. The ridges of the roof-shaped projections preferably form, as do the longitudinal base edges, concentric parts of arcs of circles whereby their length is smaller than the length of the longitudinal base edges. Due to this and due to the centered position of the ridge relative to the projection area the gable faces are shaped as sloped, upwardly projecting triangles, which not only facilitates the pressing in of the implant into the bone but also facilitates the growing of the implant onto the bone.

The arrangement of the projections is preferably symmetrical so that the frontal area seems to consist of a number of similar circle segments. The spacing between each of the segments, the spacing from the edges of the segments and the radial surface area of the projections are identical. The radial length of the longitudinal base edges of the projections increases proportionally with increasing radial distance. It has been shown that four projections arranged adjacent to each other in the radial direction in each segment and 12 segments is sufficient for anchorage and for ensuring that the conditions are good for growth onto the bone.

Particularly, a spacer made of rigid material, which cannot deform in vertebral movements and whose areas bordering the vertebrae are therefore greatly strained, can be safely secured in this manner.

The frontal areas of the endoprosthesis shaped as described above and which are to be pressed into the milled level bone surfaces are preferably coated with a porous layer of biocompatible material. Such a layer preferably comprises a so-called madreporation made from a material which is identical with the core material or a resorbable layer of polylactide or an equally suitable material—which—when applied to a porous surface—after the implantation—is replaced by newly formed bone material.

A circumferential groove running around the lateral surface area of the spacer simplifies the surgical operation. The implant can be held by and inserted using surgical forceps. Spongiosa screws, bone cement or other anchoring means are no longer required.

If, in accordance with a preferred embodiment of the invention, the frontal area has an inclination which is symmetrical relative to the middle plane and preferably of an angle between 3° or 4°, the shape of the implant corresponds more closely to the curvature of the spine in the neck region and enables insofar an optimal fit and load transmission between vertebra and implant.

In particular, a rounded recess is provided, which extends from the edge towards the centre as far as a depth of essentially 10% of the diameter. This recess forms an passage for the spinal nerve and is preferably in that part of the circumference towards which the frontal areas converge.

In order to simplify the manipulation of the implant a bore is provided which extends from the edge of the implant towards the centre and is provided with an internal thread over at least a part of its length. A setting instrument which has a rod or shaft with a corresponding external thread is provided to engage with this bore. Furthermore the instrument is provided with a displaceable casing which comprises at least one nose-shaped projection at its end facing the external thread of the shaft, the projection engaging with the recess adjacent to the bore of the implant and the recess being part of a circumferential groove of the implant. Due to a stop or a corresponding catch the screwing of the threaded part of the shaft into the bore pulls the nose-shaped projection into the recess and engages with it.

Further advantageous features of the invention are featured in the dependent claims and will be described in greater detail below, together with a description of the preferred embodiment of the invention as shown in the drawings. They show:

BRIEF DESCRIPTION OF THE DRAWINGS

FIGS. 4a to 4d are further embodiments of the endoprosthesis according to the present invention.

FIG. 5b is an elevational view of the setting instrument shown in FIG. 5a.

DETAILED DESCRIPTION OF THE INVENTION

Figure 1:
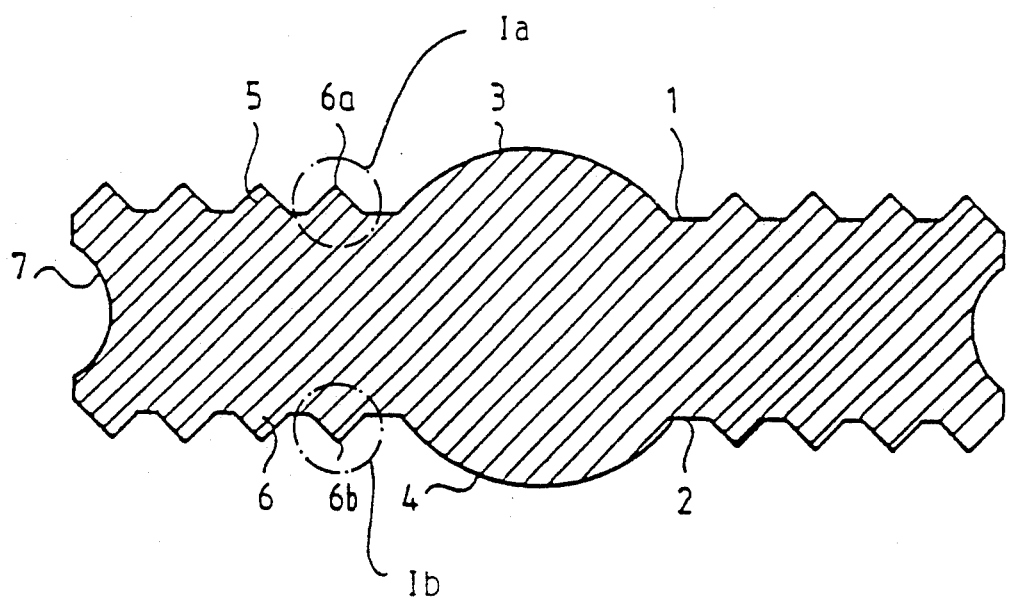
FIG. 1 is a longitudinal sectional view of an embodiment of the endoprosthesis according to the present invention.

The longitudinal section of an endorposthesis of an intervertebral disc as illustrated in FIG. 1 shows a central raised dome 3 and 4 on each of its frontal areas 1 and 2 bordering the vertebrae. Each of the raised domes 3 and 4 are surrounded by roof-shaped projections of which two, as examples, have been designated 5 and 6. The sloped, upwardly projecting edges of the projections 5 and 6 are in the form of cutting edges which facilitate the pressing of the prosthesis onto the levelly milled vertebrae. Because the inside of the vertebrae consist of soft tissue the ridges 6a and 6b of the projections 5 and 6, which extend further than the raised domes 3 and 4, can be pressed into the bone tissue. In order to be able to hold and direct the endoprosthesis with a surgical forcep the lateral surface area of the endoprosthesis has a circumferential groove 7. This groove forms a round depression in cross-section and spans approximately half of the height of the lateral surface area.

Figure 1A:
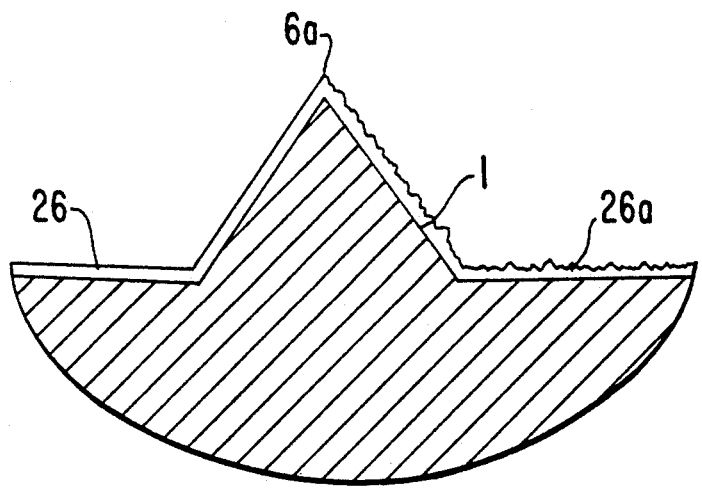
FIG. 1a is an enlarged longitudinal section view of detail I of the endoprosthesis shown in FIG. 1.
Figure 1B:
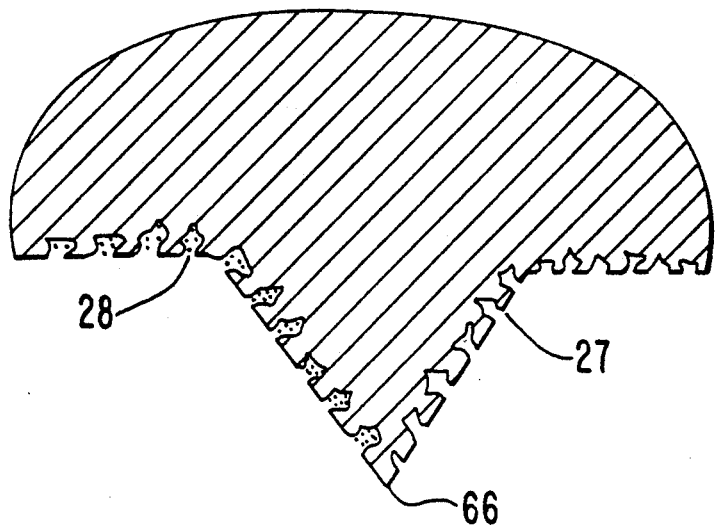
FIG. 1b is an enlarged longitudinal sectional view of detail II of the endoprosthesis shown in FIG. 1.

FIG. 1a shows an enlarged view of detail 1a of the endoprosthesis of FIG. 1. The surface of the frontal area 1 is coated with a porous biocompatible layer 26. This surface coating 26 can either be smoothly 26 or roughly structured 26a. The treated and porous surface 27 of frontal area 2 in FIG. 1b is partially filled with resorbable material 28 in order to enable the ingrowth of bone material. Such a surface treatment 27 and/or surface coating 26 serve to facilitate growth onto the bone.

Figure 2:
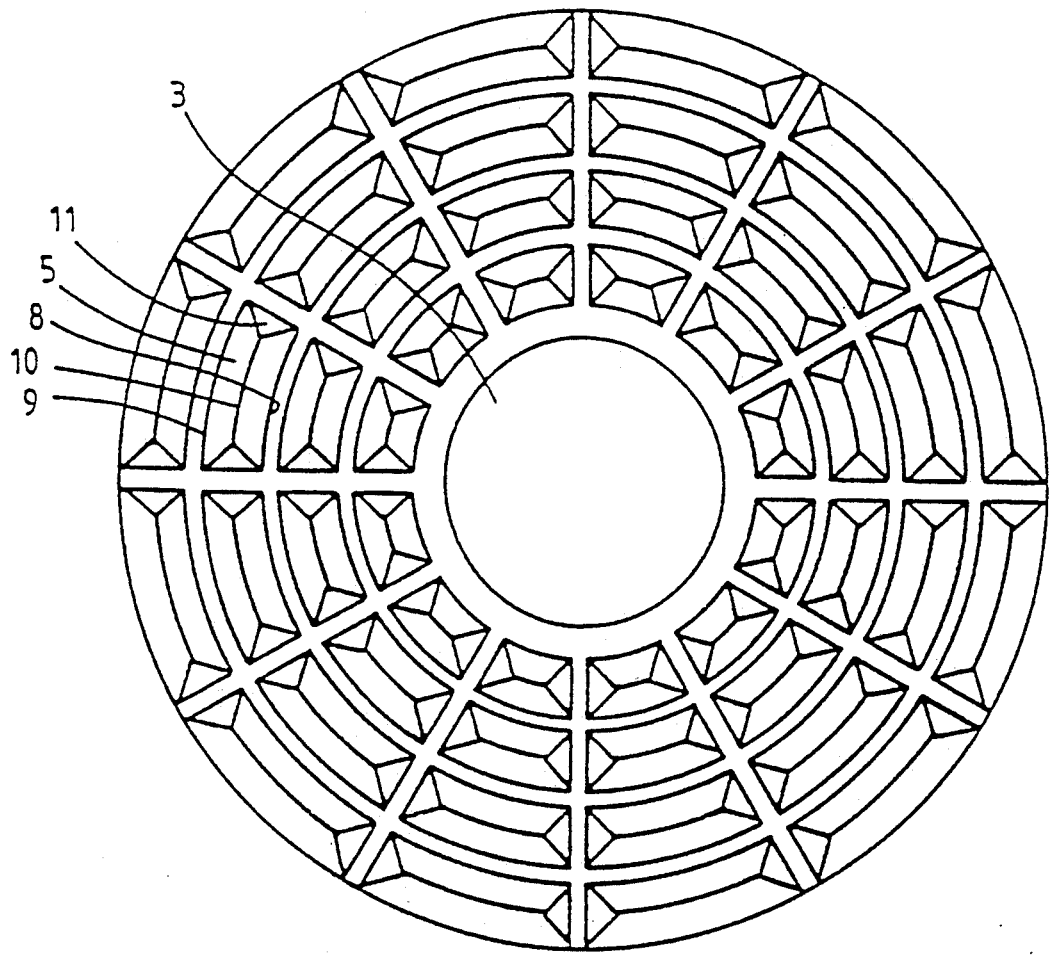
FIG. 2 is a plan view of the endoprosthesis shown in FIG. 1.

FIG. 2 shows a plan view of one of the two similarly shaped frontal areas 1 or 2 of the endoprosthesis. The round frontal area 1 or 2 is subdivided into one central region in which the raised dome 3 or 4 is situated and four ring-shaped regions which surround the raised dome 3 or 4. Twelve roof-shaped projections 5 or 6 are situated in each of the ring-shaped regions and the shape and the size of the projections 5 or 6 are the same in each of the ring-shaped regions. The surface structure of the frontal areas 1 and 2 comprises twelve identical segments. The segments, together with the raised dome 3 or 4, prevent an unintentional dislocation in any radial direction.

The longitudinal base edges 8 and 9 of the ridge 10 of the roof-shaped projections 5 or 6 form concentric arcs of circles whereby the ridge 10 is not as long as the longitudinal base edges 8 and 9. In that way, the gable end faces 11 of the roof-shaped projections 5 or 6 incline upwardly. The projections are therefore shaped like a hip roof. An unintentional rotation of the intervertebral implants can be prevented in both tangential directions due to these gable end edges.

The roof-shaped projections 5 or 6 as arcs of circles are longer with increasing distance from the center. They are symmetrically situated on radii of the round frontal areas and form a ray-like pattern. Regions lying on the same level as the frontal areas of the essentially cylindrically shaped endoprosthesis remain in between the projections.

Figure 3:
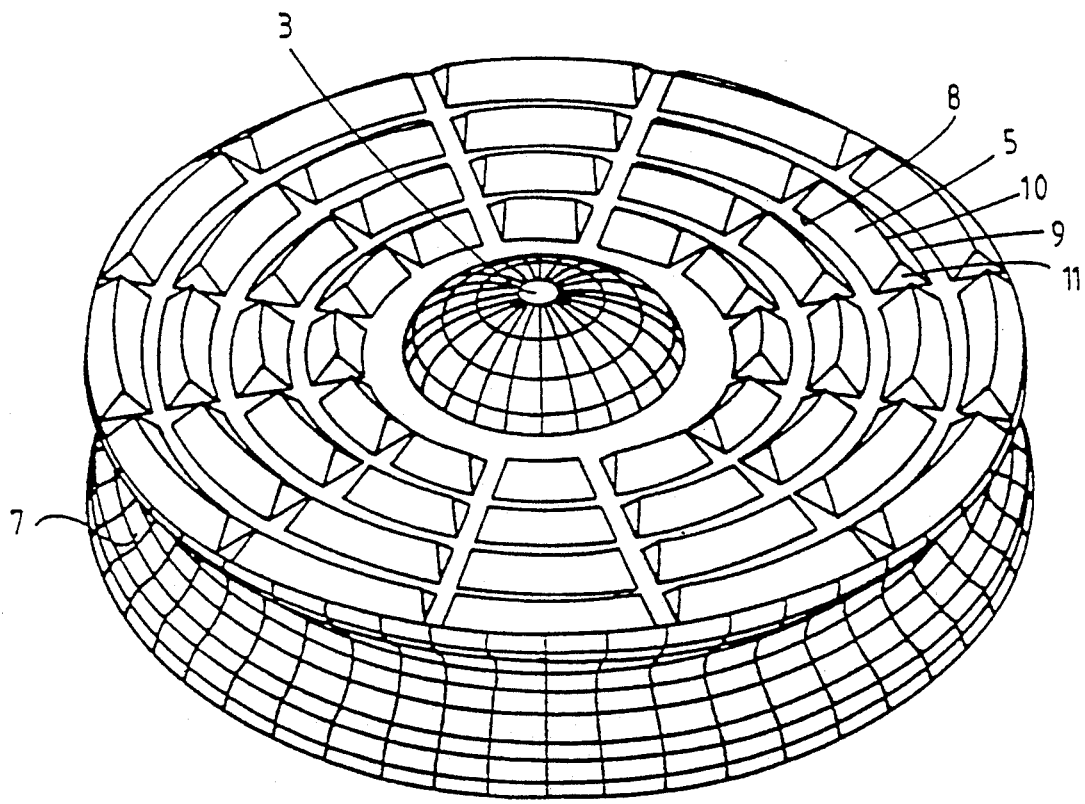
FIG. 3 is a perspective view of the endoprosthesis shown in FIGS. 1 and 2.

A perspective view of the endoprosthesis of the intervetebral disc is illustrated in FIG. 3 as a wire model in order to emphasize the surface structure.

A further variation of the intervertebral implant according to the invention is shown in the FIGS. 4a to d. The elements which correspond to those elements of the previously described embodiment are given the corresponding numerals onto which an "'" has been added.

In the sectional view of FIG. 4a it can be seen, that both frontal areas have an inclination of approx. 7° relative to each other. The direction of inclination is chosen to be symmetrical to the middle plane for both frontal areas and is therefore approx. 35° between the middle plane and each frontal area. The diameter of the implant is between 16 and 20 mm whereas the height is between approx. 6 and 9 mm. The total inclination of the frontal areas is increased with increasing diameter of the embodiments corresponding to different vertebrae sizes so that the greatest inclination corresponds to the greatest diameter and vice versa.

In the plan view according to FIG. 4b a rounded recess 12 can be seen, which has a depth of 10% of the diameter. The recess is substantially cylindrical, whereby the axis of the rounding runs parallel to the geometrical axis of the implant. The recess prevents the nerve tracts in the spinal region from being blocked by the implant. The radius of the rounding is approximately equal to half the radius of the frontal areas. As can also be seen from FIG. 4d the recess is on that side of the implant with the smallest distance between both frontal areas.

It can be seen from the sectional view according to FIG. 4a and also from the side view according to FIG. 4c that the shown implant has a bore 13 which extends beyond the middle region by about half a diameter of the dome 3' or 4'. A metrical internal thread 14a is provided between an outer enlarged area 14 and the end of the bore. The outer enlarged area 14 prevents the bone from being able to grow into the threaded bore. In addition, another cap—not shown in the FIGURE —made from an elastic biocompatible material, for example silicon rubber, is provided, with which the opening can be closed over after the implant has been inserted.

Figure 5A:
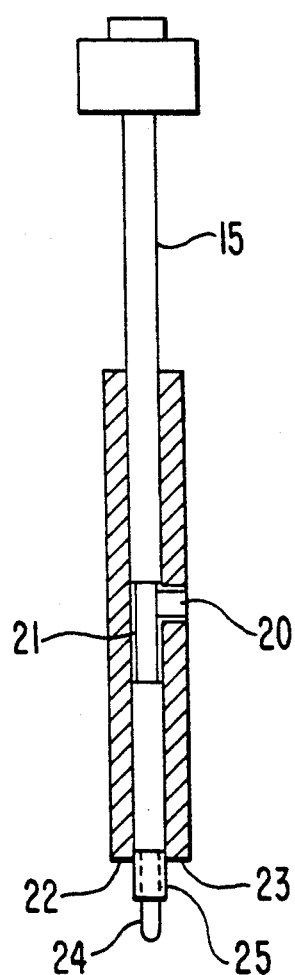
FIG. 5a is a cross-sectional view of the setting instrument according to the present invention.
Figure 5B:
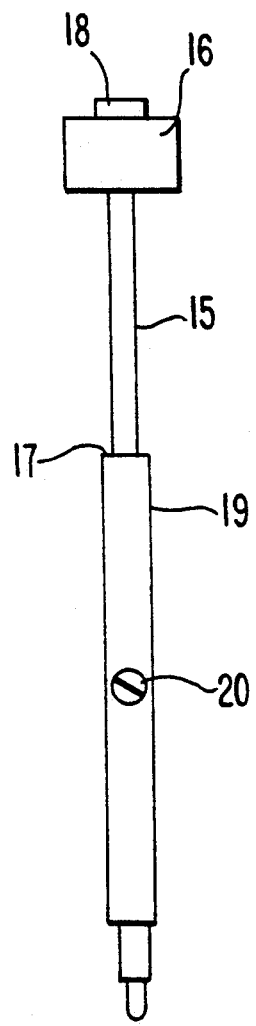

The bore serves to receive an instrument to manipulate an intervertebral implant, the instrument being shown in FIG. 5a in the plan view in section and in FIG. 5b in side view.

On a slim shaft region 15 a striking weight 16 is displaceable between two stops 17 and 18 so that an insertion or removal of the implant which is connected to such a setting instrument can take place in accordance with the strike direction.

The stop 17 is formed by the front end of a casing 19 which is longitudinally displaceable along the shaft 15 by a set distance. The casing 19 has a screw 20 which is firmly connected to the casing 19 and whose end which faces the middle axis of the casing projects into the inside of the casing. This end engages with a region 21 of the shaft 15 having a reduced diameter. In this way, the casing 19 can not be totally removed from the shaft 15. The casing is oval in cross-section and has projections 22 and 23 on the side opposite the stop 17 which grip into the corresponding recesses of the implant.

A free threadless shaft end 24 corresponds in its diameter to the bore 13 and the adjoining external thread 25 corresponds to the internal thread 14a of the bore.

To insert the implant the free end of the shaft 24 with the external thread 25 is inserted in the bore of the implant and is firmly screwed in. The noses 22 and 23 are thereby pulled into the circumferential groove of the implant and thereby make it possible for the position of the implant to be controlled by holding the casing 19. The implant can now be driven in with the set weight 16. After the final position has been reached the instrument is removed. In order to remove the implant during reoperation the steps must be carried out in the opposite order.

It will be understood that the above description of the present invention is susceptible to various modifications, changes and adaptations, and the same are intended to be comprehended within the meaning and range of equivalents of the appended claims.

We claim:

1. An intervertebral implant insertable between two vertebrae, comprising:

a disc made of rigid material and having two opposing sides bordering respectively adjacent vertebrae, each said side having a circular frontal area, a raised dome at a central portion of said circular area, and roof-shaped projections surrounding said dome, each of said projections having a pair of end faces, a ridge edge, a pair of side faces, and a pair of base edges extending between said end faces, each of side faces terminating at said ridge edge and at a respective base edge the base edges and the ridge edge of said projections forming respective arcs of concentric circles.

2. The intervertebral implant according to claim 1, wherein each of said raised domes is convex and spherically shaped, and wherein an outer diameter of each of said raised domes corresponds to an inner diameter of a marrow cavity of a respective one of the vertebrae.

3. The implant according to claim 1, wherein said end faces comprise upwardly sloped projecting triangles the ridge edge on each of said projections being shorter in length than the base edges of the same projection, and each said side having level regions between said roof-shaped projections.

4. The intervertebral implant according to claim 1, wherein the ridge edges of the projections on each side of said disc are of increasing length in a radially outward direction.

5. The intervertebral implant according to claim 1, and further comprising means for promoting bone tissue resorption located on at least portions of said circular frontal areas.

6. A rigid intervertebral implant according to claim 1, wherein said disc has a lateral surface area that is substantially cylindrical, said lateral surface area including a circumferential groove.

7. A rigid intervertebral implant according to claim 1, wherein said disc is rotationally symmetrical about a central axis.

8. The intervertebral implant according to claim 1, wherein said disc is symmetrical about a plane of symmetry mid-way between said sides.

9. The intervertebral implant according to claim 8 wherein each said frontal circular area is disposed at an angle of between 3 to 4 degrees with respect to said plane of symmetry.

10. The intervertebral implant according to claim 1, wherein said disc includes a substantially cylindrical lateral surface having a central axis and a rounded recess in said lateral surface, said rounded recess having a geometrical axis that is parallel to said central axis.

11. The intervertebral implant according to claim 10, wherein said disc has a diameter and said rounded recess extends inwardly toward said central axis to a depth of about 10% of the diameter of said disc.

12. A rigid intervertebral implant according to claim 11, wherein the sides of said disc are non-parallel relative to one another and said rounded recess is disposed at a region of said lateral surface where said sides are closest to one another.

13. The intervertebral implant according to claim 1, wherein said disc has a substantially cylindrical lateral surface defining a central axis and a bore extending inwardly from said lateral surface toward said central axis.

14. A rigid intervertebral implant according to claim 13, wherein a portion of a surface along said bore includes an internal thread.

15. An arrangement comprising the intervertebral implant according to claim 14, and a tool for manipulating said implant, said tool comprising:

(a) a shaft having one end with an external thread corresponding to the internal thread along said bore; and (b) a displaceable shaft casing surrounding said shaft and having one end adjacent to said shaft external thread and provided with at least one projection for engaging with an outer region of said bore during an insertion of said implant between two vertebrae.

16. An arrangement according to claim 14, wherein said shaft further comprises two stops and a weight displaceable between said two stops.

* * * * *